United States Patent
Johnson et al.

(10) Patent No.: US 9,480,783 B2
(45) Date of Patent: Nov. 1, 2016

(54) BREAST PUMP SYSTEM

(75) Inventors: Mark Thomas Johnson, Arendonk (BE); Nicolle Hanneke Van Schijndel, Eindhoven (NL); Rachel Estelle Thilwind, Cambridge (GB); Marjolein Irene Van Lieshout, Waalre (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 866 days.

(21) Appl. No.: 13/062,345

(22) PCT Filed: Sep. 7, 2009

(86) PCT No.: PCT/IB2009/053886
§ 371 (c)(1),
(2), (4) Date: Mar. 4, 2011

(87) PCT Pub. No.: WO2010/029483
PCT Pub. Date: Mar. 18, 2010

(65) Prior Publication Data
US 2011/0160656 A1 Jun. 30, 2011

(30) Foreign Application Priority Data
Sep. 9, 2008 (EP) .................................... 08163968

(51) Int. Cl.
*A61M 1/06* (2006.01)
*A61M 1/00* (2006.01)
(Continued)

(52) U.S. Cl.
CPC .............. *A61M 1/06* (2013.01); *A61M 1/0031* (2013.01); *A61M 1/0037* (2013.01); *A61M 21/02* (2013.01); *A61M 2021/0022* (2013.01);
(Continued)

(58) Field of Classification Search
CPC .. A61M 1/0031; A61M 1/0037; A61M 1/06; A61M 2021/0022; A61M 2021/0088; A61M 2230/00
USPC ...................................................... 604/73–76
See application file for complete search history.

(56) References Cited

U.S. PATENT DOCUMENTS 6,358,226 B1 3/2002 Ryan
6,836,681 B2 12/2004 Stabler et al.
(Continued)

FOREIGN PATENT DOCUMENTS

| EP | 1163915 A2 | 12/2001 |
| EP | 1221319 A1 | 7/2002 |
| EP | 1502610 A1 | 2/2005 |
| EP | 1586340 A2 | 10/2005 |
| WO | 0041744 A1 | 7/2000 |

OTHER PUBLICATIONS

Dewey, K.: "Maternal and Fetal Stress Are Associated With Impaired Lactogenesis in Humans"; Journal of Nutrition, Nov. 2001, vol. 131, No. 11, pp. 3012S-3015S.
(Continued)

*Primary Examiner* — Rebecca E Eisenberg

(57) ABSTRACT

A breast pump system (1) comprises a breast pump arranged to extract milk from a user; and a breathing guidance means configured to provide a suggested breathing pattern to the user. The breathing guidance means may be produced by a motorized breast pump unit (10), or may be a series of stimuli at a stimuli frequency, which are perceivable by the user. The system (1) may include a heart rate monitor for measuring the heart rate of the user, and the suggested breathing pattern may be coupled to the measured heart rate.

17 Claims, 3 Drawing Sheets

(51) Int. Cl.
    *A61M 21/02* (2006.01)
    *A61M 21/00* (2006.01)
(52) U.S. Cl.
    CPC .............. *A61M 2021/0027* (2013.01); *A61M 2021/0044* (2013.01); *A61M 2021/0066* (2013.01); *A61M 2021/0088* (2013.01); *A61M 2230/00* (2013.01); *A61M 2230/04* (2013.01); *A61M 2230/06* (2013.01)

(56) References Cited

U.S. PATENT DOCUMENTS

| | | | |
|---|---|---|---|
| 7,255,681 | B1 | 8/2007 | Silver et al. |
| 9,173,587 | B2 | 11/2015 | Van Schijndel |
| 2005/0059928 | A1 | 3/2005 | Larsson |
| 2005/0085768 | A1 | 4/2005 | Greter et al. |
| 2005/0234370 | A1 | 10/2005 | Beal et al. |
| 2011/0036801 | A1* | 2/2011 | Krans et al. ............... 215/11.1 |

OTHER PUBLICATIONS

Patterson et al: "Voluntary Cardio-Respiratory Synchronisation"; IEEE Ingineering in Medicine and Biology Magazine; Nov./Dec. 2004, vol. 23, No. 6, pp. 52-56.
Kimura C, Matsuoka M. "Changes in breast skin temperature during the course of breastfeeding". J Hum Lact. Feb. 2007;23(1):60-9.
Cox DB, Owens RA, Hartmann PE. "Blood and milk prolactin and the rate of milk synthesis in women". Exp Physiol. Nov. 1996;81(6):1007-20.
http://www.heartmath.com.
Lena Nilsson, "Respiratory monitoring using reflection mode photoplethysmography", PhD thesis nr. 898 Linkopings University 2005.

* cited by examiner

BREAST PUMP SYSTEM

FIELD OF THE INVENTION

The present invention relates to a breast pump system for extracting milk from a user.

BACKGROUND OF THE INVENTION

Breast pumps are well known devices for extracting milk from a breast of a user, for example as known from US 2005/234370. A breast pump may be used if the baby is not itself able to extract the milk, or if the mother is separated from the baby, for example if away from the baby at work. The use of a breast pump to extract milk may also be used to stimulate lactation in women with a low milk supply, or to relieve engorgement.

Breast pumps may be manually operated, for example by squeezing a handle or operation of a foot pedal. Breast pumps may also be electrically driven by a small electric motor.

The expression of milk using a breast pump may be difficult for a user. In order to effectively express milk, it is important that the user is relaxed. The hormone oxytocin plays a vital role in milk expression, and stress inhibits its release. For milk expression to occur, oxytocin is released in the blood stream, and is transported to the breast. This causes the myoepithelial cells that cover the milk glands to contract. Contraction of the cells around the milk glands and shortening of the milk ducts pushes the milk out of the glands towards the nipple where it is expressed into the breast pump.

If release of oxytocin is inhibited, the cell contraction that pushes the milk out of the glands may be disabled. When milk is not removed from the breast, an inhibitory factor signals to the body to cease production of milk, and so the milk supply can rapidly diminish.

SUMMARY OF THE INVENTION

The present invention provides a breast pump system according to claim 1. Thus, by guiding the breathing of the user the stress of the user is reduced, and by focusing on breathing the user is distracted from the purpose of milk production. This improves the ability of the user to express milk, and hence the breast pump system can operate more effectively.

BRIEF DESCRIPTION OF THE DRAWINGS

The invention will now be described, by way of example only, with reference to the accompanying drawings, in which.

DETAILED DESCRIPTION OF THE EMBODIMENTS

Figure 1:
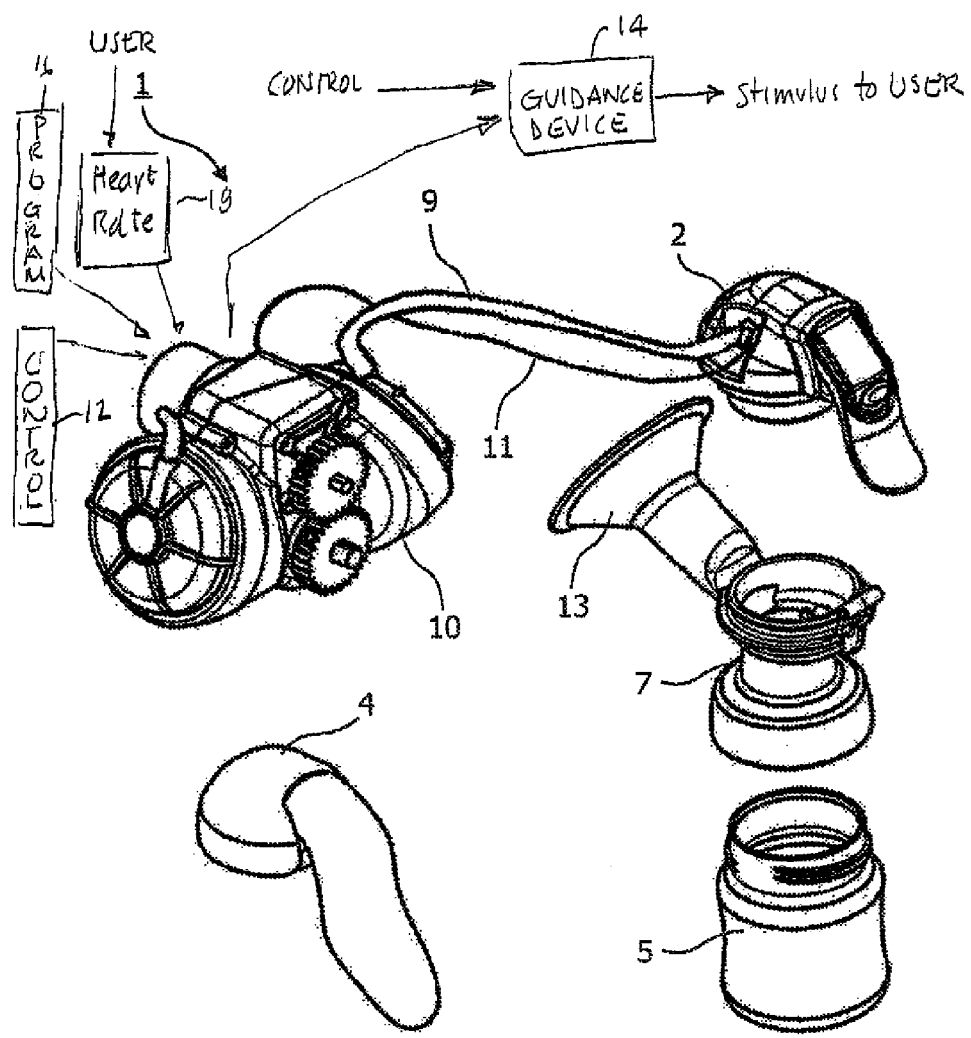
FIG. 1 is a perspective view of the breast pump of the present invention.

FIG. 1 illustrates an embodiment of a breast pump unit 1 for extracting milk from a user, forming part of the breast pump system of the present invention. The breast pump 1 includes a pump unit 10 (shown without a casing), a pump head 2, a feeding bottle 5 and a body 7. A trumpet 13 is attached to the body 7 for receiving the breast of a user. The head 2 is connected to the pump 10 by a flexible tube 9. A multi-core electrical lead 11 also extends from the head 2 to the pump 10. The body 7 can be attached to the bottle 5 by a screw fitting. Attachment of the pump head 2 to the body 7 provides a breast pump unit driven by the motorised pump unit 10. Alternatively, the system may not include a motorised pump unit. Instead, a manual head 4 can be attached to the body 7 to provide a breast pump unit which is manually operable.

The tube 9 contains a working fluid (e.g. a liquid or air) which is pumped back and forth by the pump 10 to vary the pressure within the trumpet 13. The working fluid is separated from the trumpet 13 by a flexible diaphragm. In use, when the pump unit 10 sucks air though the tube 9, or when the user actuates the manual head 4, the diaphragm is lifted, reducing the pressure within the trumpet 13 and encouraging expression of milk from the user's breast. A period of suction followed by a period of released suction (reduced suction) constitutes one cycle of the pump unit 10. During the period of released suction there is still some suction applied, the vacuum at the breast does not break to atmospheric pressure. The pumping cycle can be felt by the user through the trumpet 13. Further details of the pump 1 can be obtained from EP1,502,610. Alternatively, any other conventional powered or manually operable breast pump can be used in the system of the present invention.

The breast pump system further comprises a breathing guidance means, which is configured to guide the user to follow a suggested breathing pattern.

The function of the breathing guidance means is to provide a breathing guide for the user to follow to control, and preferably slow, the user's breathing. Breathing slowly, for example less than around 10 breaths per minute, assists in relaxing the user. The relaxation allows release of the hormone oxytocin, and hence effective expression of milk.

The breathing guidance means of the present invention can take a variety of forms to perform the function of guiding the user's breathing. In a first embodiment, the breathing guidance means is the powered breast pump unit 10 itself, configured to operate at a pumping frequency selected to provide a suggested breathing pattern. The pumping frequency is the frequency at which the pump unit completes a cycle, during which suction is applied to the nipple and then reduced. The pump unit can be operated with each cycle having a time period of around 0.5 to 30 seconds, and more preferably 2 to 10 seconds per cycle.

In a further aspect of the first embodiment, the pumping frequency is selected so that the user breathes at exactly the pumping frequency, that is, breathes in during the first pumping cycle, breathes out during the second pumping cycle, breathes in during the third pumping cycle, etc.

Alternatively, the pumping frequency may be selected to guide the user to breathe in or out on every second pumping cycle, or every third, fourth or other pumping cycle. For example, breathing in or out on every second pumping cycle would mean breathing in during the first and second pumping cycles, and breathing out during the third and fourth pumping cycle. Alternatively, the pumping frequency may be selected to guide the user to breathe in for a number n pumping cycles, and breathe out for a number m pumping cycles, where numbers n and m are integers and n is not equal to m. Alternatively, n may be equal to m. The pumping frequency intended for the user to breathe on every second or more pumping cycle will generally be higher than the pumping frequency where the user will be breathing on each pumping cycle. In particular, the user may select a fast pumping cycle because that assists in starting milk expression ("milk ejection reflex"), and then breathe on a multiple of the pump cycles.

In a further aspect of the first embodiment, the pumping frequency is selectable by the user by a control 12. The elected frequency is constant until a different frequency is . . . selected by the user. Alternatively, the pumping frequency may not be selectable by the user, and be a fixed constant frequency.

A relatively high pumping frequency may be used at the onset of use, before the milk ejection reflex. The user may find that the more rapid pumping frequency assists in starting milk expression. After the milk ejection reflex has been triggered, the frequency may decrease relatively rapidly and by a large amount.

In a still further aspect of the first embodiment, the pumping frequency may be programmed by a program device 16 to slow down gradually during operation, in particular after the milk ejection reflex. The reduction in frequency will guide the user's breathing to become progressively slower, down to a final predetermined frequency. The pumping frequency may be programmed to gradually reduce by a certain percentage compared to the initial pumping frequency, for example, to reduce by 30%. The user may select the initial frequency, which then automatically reduces over time to a final frequency. The reduction in breathing rate can produce a strong sensation of relaxation in the user.

The pumping frequency may undergo one reduction, either a large, rapid reduction at milk ejection reflex, or a gradual reduction after milk ejection reflex. The pumping frequency may be controlled to undergo both of these reductions.

The user may undergo additional milk ejection reflexes after the first milk ejection reflex. In order to assist in these further instances of milk ejection reflex, the pumping frequency may be increased to a high frequency suitable for assisting in milk expression. Thus, the pumping frequency can be changed as appropriate to encourage a milk ejection reflex and/or to encourage relaxation.

In a second embodiment of the present invention, the breathing guidance means provide a series of stimuli which are independent of the pumping frequency, and which are not provided by the pump unit 10. A breathing pattern suggested by the stimuli produced by the breathing guidance means is therefore not coupled to the pumping frequency, and is independently controllable. The series of stimuli are produced at a stimuli frequency, which may be user selectable, fixed or reducing over time. This has the advantage that the breathing pattern can be optimised for relaxation of the user, and the pumping frequency can be separately optimised for the pump to extract milk from the breast as efficiently as possible.

In this second embodiment, the pump unit 10 may be electrically driven or the pump may be manually operated. This embodiment is particularly suitable for guiding breathing when the pump is manually operable. This is because it is preferable to have one breathing pattern for the user to follow (defined by the independent stimuli), rather than the user trying to manually operate the pump unit to follow a different pumping rhythm.

The breathing guidance means may comprise a device as illustrated generally at 14 attached to a part of the pump unit 10, or it may be separate from the pump unit 10. The breathing guidance means may produce stimuli in one or more of the following forms:

Audio stimuli. Any audio signal is possible, for example the sound of waves or the sound of a or the baby. In a preferred embodiment the baby's own voice may be digitally recorded in the breast pump system. The system may comprise audio signal processing software to sample the baby's voice, and repeat the sample at the required stimuli frequency. The repetition of a sample, rather than a continuous recording, is necessary since the baby would generally not make sounds at exactly the rate required for the breathing pattern. The audio stimulus is provided at the correct frequency, without the frequency spectrum of the baby's voice being distorted (as would result by simply slowing down the playback of the recorded voice). This allows a series of stimuli to guide a slow breathing rate whilst the baby sounds remain authentic.

Visual stimuli. For example, one or more lights may indicate to the user when to breathe in and out, using, for example, changing colours or intensities.

In combination with a sound of the baby, moving images of the baby may be displayed on a screen. The moving images may be modified so that movement of the baby provides stimuli at the required rate.

Mechanical stimuli. For example, the system may comprise a stimulus part in physical contact with the user, which transmits vibrations, pressure pulses/transients, or stroking motions to the user to indicate the breathing pattern.

Heat stimuli. A heating part may be provided for contact with the user, or to be placed in close proximity to the user, to provide a pulse of heat to indicate the breathing pattern.

The pumping frequency may be controlled to undergo one or both of a large, rapid reduction at milk ejection reflex, or a gradual reduction after milk ejection reflex, as described for the first embodiment. The pumping frequency may also be increased.

In a third embodiment of the present invention, the breathing guidance means provides stimuli to guide the user to follow a suggested breathing pattern, the stimuli being additional to the powered pump unit. The stimuli may be of any type as described in the second embodiment above e.g. audio stimuli. The stimuli in this embodiment are synchronous with the pumping frequency, and their timing coupled to the pumping frequency. The user is guided to breathe primarily by the series of stimuli. This simplifies the experience of the user, since although the pumping frequency does not provide the suggested breathing pattern; the user may be distracted by an unrelated pumping frequency.

In further embodiments of the breast pump system, the breast pump system comprises a heart rate monitor 18 to measure the heart rate of the user. The heart rate monitor may measure the heart rate using any known technique, including:

Measuring the ECG signal with electrical Ag/Ag Cl electrodes

Recording the ballistocardiogram, for example, with a static charge sensitive bed (SCSB), a piezo foil, or an EMFi-film sensor built into a chair.

Measuring the oxygen saturation.

Measuring the (photo-) plethysmogram (PPG) in the finger, ear or elsewhere.

Using non-galvanic capacitive electrodes

Using seismosomnography (SSG).

Using Ultra Wide Band radar.

Using Optical Vibrocardiography.

Using phonocardiography (using a microphone).

Using sensors incorporated in worn textiles or underwear, or sensors on the wrist of a user.

Preferably, the heart rate sensor is incorporated in a part of the pumping system in intimate contact with the body of the user, e.g. the trumpet 13. Alternatively, the heart rate sensor may be attached to the pump unit 10 or any part of the system 1, or may be in wireless communication with the rest of the system 1.

Figure 2A:
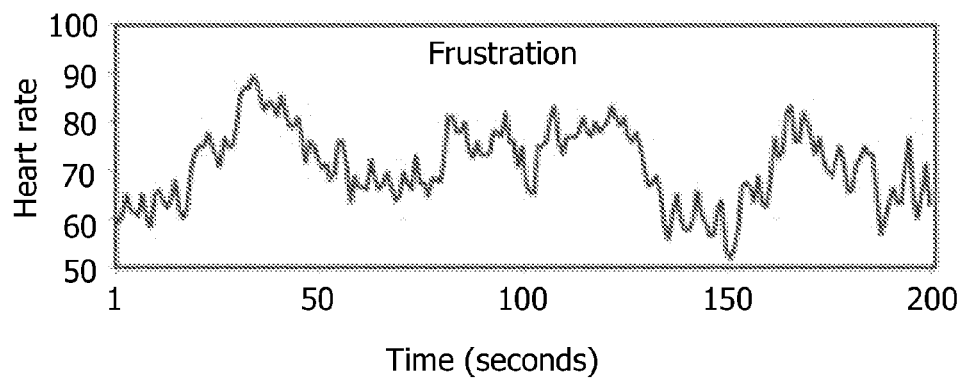
FIGS. 2a and 2b show variation in heart rate over time in different emotional states.
Figure 2B:
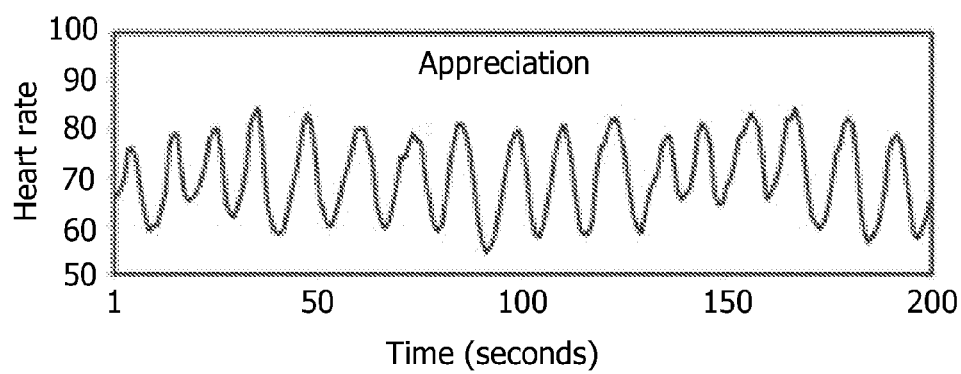

FIGS. 2a and 2b illustrate how relaxation can be assessed by monitoring a variation in heart rate over time. In FIG. 2a, the user is not relaxed and may be feeling frustrated. In FIG. 2b, the user is relaxed. The time period between successive heart rate beats is found to increase and decrease in a smooth manner, which is fixed to the breathing rate. This is known as a "coherent state". The coherent state shown in FIG. 2b, which can be induced by the breast pump system 1, has been found to be advantageous for expressing milk and so make the breast pump 1 more effective.

In a fourth embodiment, the pumping frequency of the motorised pump unit 10 is variable, and is linked to the measured heart rate. The breathing guidance means is the pump unit 10, and in particular, the pumping frequency of the pump unit 10. The pumping frequency is selected to form a breathing pattern for the user, and is controlled to be synchronous with the heart rate recorded by the heart rate monitor. The pump unit can be operated with each cycle having a time period of around 0.5 to 30 seconds, and more preferably 2 to 10 seconds per cycle. The pumping frequency, as the breathing guidance stimulus, is phased locked to the measured heart beats of the user.

Thus, a relatively high initial heart rate will cause the pump unit 10 to operate at a relatively high pumping frequency, which will guide the user to breathe at an appropriate relatively fast rate. As the user begins to relax, the heart rate will fall and so the pumping frequency will also fall, guiding the user to breathe more slowly. This will encourage the user to further relax and hence have a still lower heart rate.

The pumping frequency coupled to the heart rate may be selected to guide the user to breathe on every pumping cycle, every second pumping cycle, or on every third, fourth or higher pumping cycle as described above. Alternatively, the pumping frequency may guide the user to breathe in for n cycles and out for m cycles, where n and m are integers and not equal to each other. Alternatively, n may be equal to m. In particular, the user may select a fast pumping cycle because that assists in starting milk expression ("milk ejection reflex"), and then breath on a multiple of the pump cycles.

Figure 3:
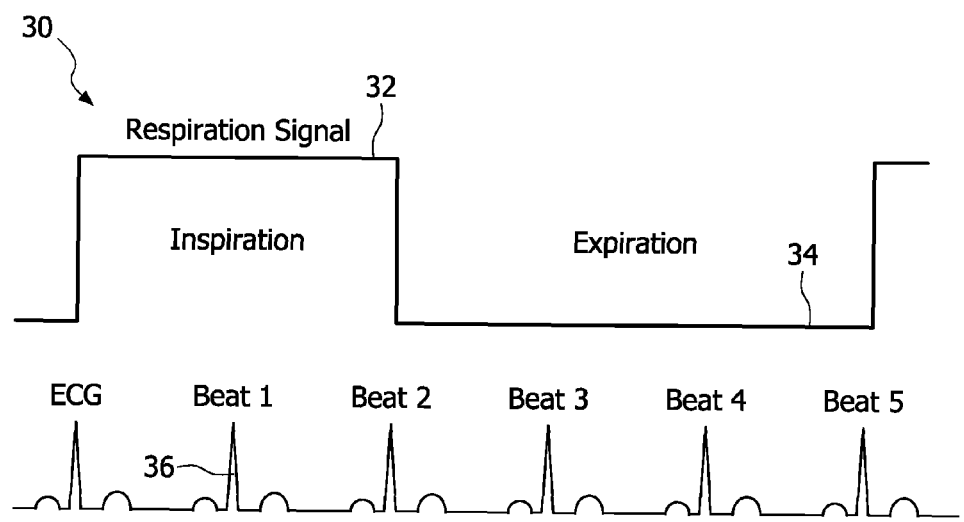
FIG. 3 is a schematic diagram illustrates a first timing pattern of an embodiment of the present invention.

FIG. 3 illustrates a breathing pattern 30 linked to the heart beats 36, where the pattern is to breathe in (inspiration) for a period 32 of two heart beats, and then to breathe out (expiration) for a period 34 of three heart beats. The breathing pattern 30 is indicated by the cycles of the pump 1 in the fourth embodiment, i.e. a pump cycle starts at the point inspiration should begin, and the next pump cycle starts at the point expiration should begin. The periods 32,34 of inspiration and expiration coincide with heart beats.

Figure 4:
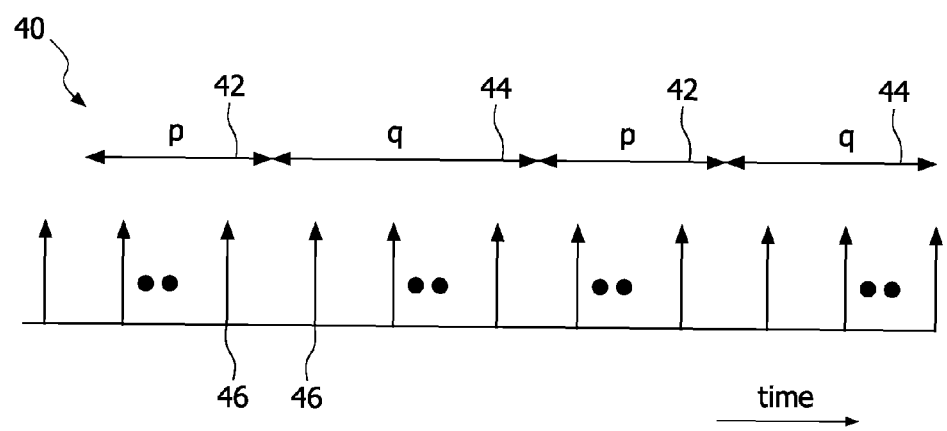
FIG. 4 illustrates a second timing pattern according to a further embodiment of the invention.

FIG. 4 illustrates an alternative breathing pattern 40 linked to heart beats 46. The pattern is to breathe in during a number p heart beats during a period 42, and to breathe out for a number q heart beats during a period 44. The period 42 is two heart beats in length, and the period 44 is three heart beats in length. The breathing pattern 40 is indicated by the cycles of the pump 1 in the fourth embodiment. The start and end of the periods 42,44 do not necessarily coincide with the heart beats.

The breathing does not have to be exactly in synchronisation with the heart rate, the effect can be achieved if the breathing and heart rate are approximately in sync. In particular, from the theory of weakly coupled systems it is know that if $|n\phi_H - m\phi_R| < \epsilon$, where n and m are integers, $\phi_H$ and $\phi_R$ are the phases of the heart and respiratory signals respectively, and $\epsilon$ is a sufficiently small constant number the signals can be considered as phase locked. The system thus employs a voluntary cardio-respiratory synchronisation (VCRS) method to achieve coherence of the heart beat, and encourage relaxation. Further details of VCRS are found in the paper "Voluntary cardio-respiratory synchronisation", R. B. Patterson, A. Belalcazar and Pu Yachuan, IEEE Engineering in Medicine and Biology Magazine, 23(6), pp 52-56, November/December 2004 and "Maternal and Fetal stress are associated with impaired lactogenesis in humans", Dewey K. G, J. Nutr. 2001 November; 131(11):3012S-5S. The synchronisation of breathing with the heart rate has been found to obtain a strongly coherent heart rate variability, as illustrated in FIG. 2b.

The phase difference between the heart pulses and the start of inhalation and exhalation provides some freedom to the user in breathing. This avoids the user being frustrated by a timing guide which does not feel right. Furthermore, the independence of the exact timing of the breathing pattern to the heart beats may be advantageous if the monitored heart beats are registered with a delay from the actual heart beat, for example as may occur if the monitor is a (photo-) plethysmogram (PPG) from a finger of the user. The periods 42,44 may not be an integer number of heart beats, and so may have a length including a sub-multiple of a heart beat e.g. the length of one or both of the periods 42,44 may be 2.5 heart beats. The number of heartbeats p,q in each period may be selected by the user, or automatically varied by the system in response to measurements of the heart rate.

The timing of the heart beats in the embodiments of FIG. 3 or 4 may by predicted with an Auto Regressive (AR) filter. In the event that the signal from the heart rate monitor is unreliable, the AR function can predict the correct timing.

The initial time periods 32,34,42,44 for breathing in and out may be determined by allowing the user to breathe in and out at her own pace, and determining the breathing pace from the monitored heart rate. The time periods may then be set to be the same as the user is naturally breathing at, and the time periods 32,34,42,44 may then be gradually increased over time.

The pumping frequency may be controlled to undergo a large, rapid reduction at milk ejection reflex, and then be coupled to the heart rate after the milk ejection reflex.

In a fifth embodiment, a stimulus additional to the pump unit 10 provides a guide to a breathing pattern. The additional stimulus may be any of the stimuli mentioned with reference to the second embodiment, e.g. audio, visual, mechanical and/or heat stimuli. The stimuli are produced with a frequency which is coupled to the measured heart rate of the user. The breathing guidance stimulus frequency is substantially phase locked to the measured heart beats of the user. The stimuli frequency is independent of the pumping frequency of the pump unit, or independent of the manual operation of the pump.

The breathing pattern may be as shown in FIGS. 3 and 4, with the series of stimuli indicating the periods of breathing in and breathing out.

In a sixth embodiment, an additional series of stimuli are provided to guide the breathing of the user. The additional stimuli are synchronous with the pumping frequency. Both the additional stimulus frequency and the pumping frequency are variable and linked to the measured heart rate of the user. This embodiment is thus analogous to the third embodiment, with the pumping frequency and stimuli frequency being coupled to the measured heart rate. The breathing pattern may be as shown in FIGS. 3 and 4, with the series of stimuli and pumping cycles indicating the periods of breathing in and breathing out.

The pumping frequency coupled to the heart rate may be selected to guide the user to breathe on every second pumping cycle, or on every third or fourth pumping cycle as described above, or to breathe in for n cycles and out for m cycles, where n and m are integers and not equal to each other. The stimuli may indicate the time to start breathing in and start breathing out only, even if the pump unit is operating at a faster rate, i.e. a multiple of the stimuli frequency.

Embodiments four to six assist a user in enabling a relaxed state, in which their heart rate is in a coherent state. Once in the coherent state, the user may find it beneficial to breathe at a rate different from the suggested heart rate. In a seventh embodiment, the system may allow the user to switch off any additional stimuli when in the coherent state, or the system may automatically switch off the additional stimuli when the system determines the user is in a coherent state (above a threshold level), optionally after the user has been in the coherent state for a pre-determined amount of time. The system continues to monitor the user's heart rate using the heart rate monitor, and provide feedback to the user of the level of coherence. This feedback may be done by audio or visual cues, for example. If the system senses that the user's heart rate is no longer in a coherent state (below the threshold level), or coherence is reducing, the system may revert to providing the additional stimuli as described in embodiments five or six, or the pumping rate again may become phase locked to the measured heart rate of the user as described in embodiment four.

In association with any of embodiments four to seven, the system may continually provide feedback to the user about her relaxation state, using the heart rate monitor to determine heart rate variability and the associated coherence level. The feedback may be in the form of audio or visual cues. This information may be of use to the user to understand why there are problems expressing milk.

The features of any of the described embodiments may be used with the features of any one or more of the other embodiments. The features of the embodiments may therefore be used in isolation, or in combination with any one or more features of one or more of the other embodiments.

The invention claimed is:

1. A breast pump system, comprising:
   a breast pump arranged to extract milk from a user; and
   a breathing guidance means configured to provide a suggested breathing pattern to the user timed for a selected breathing rate for the user to facilitate release of oxytocin in the user.

2. A breast pump system as claimed in claim 1 wherein the breast pump comprises a breast pump unit motorised to operate at a pumping frequency; and
   the breast pump unit is the breathing guidance means and the pumping frequency provides the suggested breathing pattern.

3. A breast pump system as claimed in claim 2 wherein the pumping frequency is controlled to be constant, or, the pumping frequency is controlled to change from a first frequency to a second frequency.

4. A breast pump system as claimed in claim 3 wherein the pumping frequency is controlled to reduce rapidly once a milk ejection reflex has been triggered, and/or, the pumping frequency is controlled to reduce gradually over period of time.

5. A breast pump system as claimed in claim 2 wherein the pumping frequency is variable and coupled to a measured heart rate.

6. A breast pump system as claimed in claim wherein the breathing guidance means produces a series of stimuli at a stimuli frequency, which are perceivable by the user to form the suggested breathing pattern.

7. A breast pump system as claimed in claim 6 wherein the stimuli are at least one of audio, visual, touch or heat stimuli.

8. A breast pump system as claimed in claim 6 wherein the stimuli frequency is controllable independently of the breast pump.

9. A breast pump system as claimed in claim 6 wherein the breast pump comprises a breast pump unit motorised to operate at a pumping frequency, and the stimuli are produced at a stimuli frequency which is coupled to the pumping frequency.

10. A breast pump system as claimed in claim 9 wherein the pumping frequency and stimuli frequency are coupled to a measured heart rate.

11. A breast pump system as claimed in claim 6 wherein the stimuli frequency is coupled to a measured heart rate.

12. A breast pump system as claimed in claim 1 wherein the breast pump system includes a heart rate monitor for measuring the heart rate of the user.

13. A breast pump system as claimed in claim 12 wherein the system further comprises a feedback unit arranged to provide feedback to the user on a coherence state of the user's heart rate.

14. A breast pump system as claimed in claim 12 wherein in a first state when the heart rate monitor detects coherence above a threshold level, the breathing guidance means is configured not to produce any stimuli, and in a second state when the heart rate monitor detects coherence below a threshold level, the breathing guidance means is configured to produce the series of stimuli.

15. A breast pump system as claimed ire claim 1 wherein the breast pump comprises:
   a pump unit;
   a handheld unit for receiving a breast of the user and capturing expressed milk;
   a tube connecting the pump unit to the handheld unit and containing a working fluid which is pumped back and forth by the pump unit for varying the pressure within a part of the handheld unit.

16. A method of operating breast pump system as claimed in claim 1, comprising:
   operating the breast pump in order to extract milk; and
   breathing substantially in time with the breathing pattern provided by the breathing guidance means.

17. A breast pump system as claimed in claim 1 wherein the breathing rate is less than 10 breaths per minute.

* * * * *